United States Patent
Levy et al.

(10) Patent No.: US 8,586,560 B2
(45) Date of Patent: Nov. 19, 2013

(54) EXON SKIPPING THERAPY FOR DYSFERLINOPATHIES

(75) Inventors: Nicolas Levy, Marseille Cedex (FR); Martin Krahn, Marseille Cedex (FR); Marc Bartoli, Marseille Cedex (FR); Luis Garcia, Paris Cedex (FR)

(73) Assignees: Institut National de la Sante et de la Recherche Medicale (INSERM), Paris (FR); Universite de la Mediterranee—Aix Marseille II, Marseilles (FR)

( * ) Notice: Subject to any disclaimer, the term of this patent is extended or adjusted under 35 U.S.C. 154(b) by 0 days.

(21) Appl. No.: 13/501,892

(22) PCT Filed: Oct. 18, 2010

(86) PCT No.: PCT/EP2010/065606
§ 371 (c)(1),
(2), (4) Date: May 4, 2012

(87) PCT Pub. No.: WO2011/054659
PCT Pub. Date: May 12, 2011

(65) Prior Publication Data
US 2012/0208865 A1 Aug. 16, 2012

Related U.S. Application Data

(60) Provisional application No. 61/252,228, filed on Oct. 16, 2009.

(51) Int. Cl.
*C12N 15/11* (2006.01)
*C12N 15/00* (2006.01)

(52) U.S. Cl.
USPC .................................... 514/44 A; 435/455

(58) Field of Classification Search
None
See application file for complete search history.

(56) References Cited

U.S. PATENT DOCUMENTS 6,673,909 B1 * 1/2004 Brown et al. ............... 536/23.1

FOREIGN PATENT DOCUMENTS

| WO | 2004/083432 A1 | 9/2004 |
| WO | 2004/083446 A2 | 9/2004 |
| WO | 2006/112705 A2 | 10/2006 |

OTHER PUBLICATIONS

Sinnreich et al, Lariat branch point mutation in the dysferlin gene with mild limb-girdle muscular dystrophy, 2006, Neurology, vol. 66, 7: 1114-1116.*

* cited by examiner

*Primary Examiner* — Tracy Vivlemore
*Assistant Examiner* — Kate Poliakova
(74) *Attorney, Agent, or Firm* — Whitham, Curtis, Christofferson & Cook, P.C.

(57) ABSTRACT

The present invention relates to methods for restoring the function of a mutated dysferlin comprising the step of preventing splicing of one or more exons which encode amino acid sequences that cause said dysferlin dysfunction. Particularly, the splicing of exon 32 is prevented. The present invention also relates to a method for treating a dysferlinopathy in a patient in need thereof, comprising the step of administering to said patient antisense oligonucleotides complementary to nucleic acid sequences that are necessary for correct splicing of one or more exons which encode amino acid sequences that cause said dysfunction. Particularly, the splicing of exon 32 is prevented.

5 Claims, 3 Drawing Sheets

SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: Oligonucleotide

<400> SEQUENCE: 1
gggaaccgct accatctacg c         21

```
<210> SEQ ID NO 2
<211> LENGTH: 22
<212> TYPE: DNA
<213> ORGANISM: Artificial
<220> FEATURE:
<223> OTHER INFORMATION: Oligonucleotide

<400> SEQUENCE: 2
ctacatgtac caggcccggg ac                                              22
```

EXON SKIPPING THERAPY FOR DYSFERLINOPATHIES

CROSS-REFERENCE TO RELATED APPLICATIONS

This application is a Rule 371 application of PCT/EP10/6506 filed Oct. 18, 2010, and claims priority to U.S. Provisional Application 61/252,228 filed Oct. 16, 2009.

FIELD OF THE INVENTION

The present invention relates to the treatment of dysferlinopathies. Particularly, exon skipping strategy is used.

BACKGROUND OF THE INVENTION

Muscular dystrophies are a heterogeneous group of disorders characterized by muscle weakness and wasting. Current treatments of this kind of pathologies consist in clinical management of symptoms.

However, for the most common muscular dystrophy, Duchenne dystrophy, several promising strategies are emerging. Particularly, the exon skipping therapy has shown hopeful results in the effective treatment and regeneration of dystrophic muscle.

Dysferlinopathies are autosomal recessive diseases of the group of muscular dystrophies comprising Limb Girdle Muscular Dystrophy type 2B and Miyoshi myopathy. Dysferlinopathies are caused by mutations in the DYSF gene located in the chromosome region 2p13.1-13.3. This gene includes 55 exons in its most characterized form (GenBank NM_003494.2), and different isoforms through the existence of alternative exons 1 of DYSF-v1 (GenBank DQ267935), exon 5a (GenBank DQ976379) and exon 40a (GenBank EF015906). The DYSF gene encodes the dysferlin protein, which is implicated in sarcolemmal repair. There are currently no real treatments for these dysferlinopathies whereas only symptoms are managed.

In 2006, Sinnreich et al. reported a patient case presenting a particularly mild phenotype of dysferlinopathy. This patient was the mother of two severely affected sisters, both homozygous for a dysferlin null mutation. Their mother was a compound heterozygous for the same null mutation, and, in addition, carried a lariat branch point mutation in intron 31 leading to an in-frame skipping of exon 32. Because she presented with only a mild proximal weakness and remained ambulant even after 70 years of age, it is most likely that the exon 32 skipped-allele may partially complement the null mutation in trans.

SUMMARY OF THE INVENTION

The present invention relates to a method for restoring the function of a mutated dysferlin comprising the step of preventing splicing of one or more exons which encode amino acid sequences that cause said dysferlin dysfunction.

The invention also provides antisense oligonucleotides complementary to a nucleic acid sequence of DYSF gene that is necessary for correct splicing of one or more exons which encode amino acid sequence of dysferlin implicated in dysfunction of a mutated dysferlin, and use thereof for the treatment of dysferlinopathies.

The invention further relates to a method for treating a dysferlinopathy caused by a dysfunction of a mutated dysferlin in a patient in need thereof, comprising the step of administering to said patient antisense oligonucleotides complementary to nucleic acid sequences that are necessary for correct splicing of one or more exons which encode amino acid sequences that cause said dysfunction, said antisense oligonucleotides being administered in an amount sufficient to cause skipping of said one or more exons during splicing.

The invention relates to a pharmaceutical composition containing the antisense oligonucleotide of the invention for the treatment of a dysferlinopathy.

DETAILED DESCRIPTION OF THE INVENTION

The inventors hypothesized that exon-skipping strategy could be used for the treatment of dysferlinopathies and considered the exon 32 as a preferential target for demonstration of the efficiency of exon skipping in dysferlinopathy therapy, as suggested by the clinical case described in Sinnreich et al., 2006.

Definitions

Throughout the specification, several terms are employed and are defined in the following paragraphs.

The term "protein dysfunction" refers to a loss of function of a protein inducing an abnormal phenotype. Protein dysfunction is generally due to a mutation leading to loss or lack of activity of the protein, unstability (increased degradation) or loss (or absence) of expression of the protein.

The term "antisense oligonucleotide" refers to a single strand of DNA or RNA that is complementary to a chosen sequence. Antisense RNA can be used to prevent protein translation of certain mRNA strands by binding to them. Antisense DNA can be used to target a specific, complementary (coding or non-coding) RNA.

The term "dysferlin" has its general meaning in the art and refers to a protein encoded by the DYSF gene and implicated in skeletal muscle repair. The term may include naturally occurring "dysferlin" and variants and modified forms thereof. The dysferlin can be from any source, but typically is a mammalian (e.g., human and non-human primate) dysferlin, particularly a human dysferlin. An exemplary native human dysferlin amino acid sequence is provided in GenPept database under accession number NP_003485 and an exemplary native human nucleotide sequence encoding for dysferlin is provided in GenBank database under accession number NM_003494.

In the context of the invention, the term "patient" refers to any subject, preferably a mammal, and more preferably a human, afflicted with a dysferlinopathy.

In its broadest meaning, the term "treating" or "treatment" refers to reversing, alleviating, inhibiting the progress of, or preventing the disorder or condition to which such term applies, or one or more symptoms of such disorder or condition.

The term "reference" or "control" refers to a subject (or a sample obtained from said subject) who has no dysferlinopathy or any other myopathy.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Exon Skipping Strategy

As will be understood by those of skill in the art, in the cell nucleus, eukaryotic genes are transcribed into pre-messenger RNA (pre-mRNA) which contains both exons and introns. To form mature mRNA, splicing occurs at specific sequences at the borders of exons and introns (splice sites) thereby removing introns and connecting exons to one another to form mRNA, which is translated into protein. Exons can be specifically targeted to prevent their inclusion in mRNA using antisense oligonucleotides having sequences that are specifically complementary to sequences within or at the borders of a targeted exon e.g. complementary to splice donor or acceptor sites, or binding sites for co-factors implicated in the splicing process, which may include sequences internal to an exon or external and adjacent (usually 5') to an exon. By annealing to these sequences, they interfere with the splicing machinery e.g. by overlapping and masking intron/exon splice junctions, thereby modifying splicing reactions so that the targeted exons are not included in the mature mRNA, i.e., the targeted exons are "skipped". The mRNA thus no longer contains the information of the skipped exon(s) and the protein it encodes does not contain an amino acid sequence corresponding to the skipped exon(s).

Accordingly, in the present specification, the expression "preventing splicing of one (or more) exon(s)" refers to the induction of a targeted deletion of said exon(s) in mature mRNA by a modification of splicing using the exon skipping strategy.

The invention thus provides methods for restoring the function of mutated proteins of interest using exon skipping technology. The method involves blocking or preventing the incorporation into mature mRNA of one or more targeted exon(s) which encodes amino sequences that are responsible for the protein dysfunction. This is accomplished by exposing the pre-mRNA that includes exons encoding the protein to antisense oligonucleotides (AONs) which are complementary to sequence motifs that are required for correct splicing of the one or more targeted exons. The AONs bind to complementary required sequences in the pre-mRNA and prevent normal splicing. Instead, the targeted exons are not included in the mature mRNA that is translated into protein, and the amino acid sequences encoded by the targeted exons are missing from the translated protein.

A first object of the present invention relates to a method for restoring the function of a mutated dysferlin comprising the step of preventing splicing of one or more exons which encode amino acid sequences that cause said dysferlin dysfunction.

In a particular embodiment of the invention, said method for restoring the function of a mutated dysferlin comprises the step of preventing splicing of a region comprising or consisting of exon 32 of the DYSF gene.

The invention thus provides methods of restoring partial or complete functionality to dysferlin, e.g. an unstable, defective, dysfunctional, not enough functional or non-functional dysferlin. Said dysferlin is typically a mutant dysferlin, the function of which is attenuated or eliminated by one or more mutations.

Those of skill in the art will recognize that there are many ways to determine or measure a level of functionality of a protein, and to determine a level of increase or decrease of functionality e.g. in response to a treatment protocol. Such methods include but are not limited to measuring or detecting an activity of the protein, etc. Such measurements are generally made in comparison to a standard or control or "normal" sample. In addition, when the protein's lack of functionality is involved in a disease process, disease symptoms may be monitored and/or measured in order to indirectly detect the presence or absence of a correctly functioning protein, or to gauge the success of a treatment protocol intended to remedy the lack of functioning of the protein.

Particularly, the functionality of dysferlin can be measured by several methods recognized in the art. For example, a membrane repair assay, based on membrane wounding of transduced isolated muscle fibers or cultured myotubes, with a two-photon laser-scanning microscope in the presence of a dye which becomes fluorescent at contact with lipid membrane and intra-cellular compounds, allows to evaluate the membrane repair/resealing capacity by evaluating the penetration and/or diffusion of the dye in the muscle fiber or cultures myotubes after membrane wounding (as described by Bansal et al., 2003, Nature).

In the present case, AONs are used to cause exon skipping resulting in an amelioration of dysferlinopathy symptoms (i.e. restoration of protein function or stability) in the range of at least about 10%, preferably about 20%, 30%, 40%, 50%, 60%, 70%, 80%, 90% or even 100%, compared to a non-treated patient case. Such symptoms may be observed on a micro level (i.e. restoration of protein expression and/or localisation evaluated by immunohistochemistry, immuno fluorescence, Western-blot analyses; amelioration of dystrophic features of muscle tissue evaluated by histological examination; restoration/amelioration of protein functionality evaluated in example by a laser-membrane-wounding assay as described above) or on a macro level (i.e. amelioration/restoration of clinical symptoms such as muscle weakness, muscle atrophy, blood Creatine Phosphokinase levels).

Those of skill in the art will also understand that the removal of exons should generally be carried out conservatively and that preferably, non-essential exons will be targeted. So long as the skipped exons are otherwise not essential to the functioning of the dysferlin, then the resulting shorter protein can still perform its role in sarcolemmal repair.

Furthermore, exons that may be considered non-essential generally include any exon (or combinations of exons) which if deleted results in maintenance of the reading frame.

According to the present invention, one or more exons may be removed in order to restore the functionality of a mutated dysferlin. If more than one exon is removed, the exons that are removed may be contiguous or they may not be contiguous, as long as the resulting mRNA retains a correct open reading frame. Further, more than one exon refers to two or more, e.g. 3, 4, 5, 6, 7, 8, 9, 10 or more exons that may be beneficially removed.

Those of skill in the art will recognize that the selection of exons for removal as described herein will usually be predicated on the expectation of a beneficial result such as restoration of the protein functionality.

Generally, the removal of exon-encoded sequences from a dysferlin protein is carried out using anti-sense oligonucleotides (AONs). Oligonucleotides are designed to complement suitable sequences, usually RNA sequences within the pre-mRNA molecule which are required for correct splicing of the targeted exon(s), thereby blocking splicing reactions that would incorporate the targeted exon(s) into mature mRNA. An AON typically binds to the sequence which it complements and sterically hinders the splicing reaction. Sequences are selected so as to be specific, i.e. the AON's are complementary only to the sequences of the pre-mRNA and not to other nucleic acid sequences. The AON's used in the practice of the invention may be of any suitable type, e.g. oligodeoxyribonucleotides, oligoribonucleotides, morpholinos, tricyclo-DNA-antisense oligonucleotides, U7- or U1-mediated AONs or conjugate products thereof such as peptide-conjugated or nanoparticle-complexed AONs. AONs employed in the practice of the invention are generally from about 10 to about 30 nucleotides in length, and may be for example, about 10 or fewer, or about 15, or about 20 or about 30 nucleotides or more in length. The binding affinity of the AON's for a targeted complementary sequence is generally in the range of from about 15 to about 25 nucleotides long depending on the chemical backbone used and on the target sequence. Typically, morpholino-AONs are about 25 nucleotides long, 2'PMO-AONs are about 20 nucleotides long, and tricyclo-AONs are about 15 nucleotides long.

A further object of the invention relates to an antisense oligonucleotide complementary to a nucleic acid sequence of DYSF gene that is necessary for correct splicing of one or more exons which encode amino acid sequence of dysferlin implicated in dysfunction of a mutated dysferlin.

In a particular embodiment, the invention relates to an antisense oligonucleotide of the invention wherein said antisense oligonucleotide is complementary to a nucleic acid sequence comprising or consisting of exon 32 of the DYSF gene or nucleic acid sequences required for correct splicing of a region comprising or consisting of exon 32 of the DYSF gene.

In a more particular embodiment, said antisense oligonucleotide is complementary to the nucleic acid sequence SEQ ID NO:1 or SEQ ID NO:2.

```
                                        SEQ ID NO: 1
                    GGGAACCGCTACCATCTACGC

SEQ ID NO: 2
                    CTACATGTACCAGGCCCGGGAC
```

For use in the instant invention, the AONs of the invention can be synthesized de novo using any of a number of procedures well known in the art. For example, the b-cyanoethyl phosphoramidite method (Beaucage et al., 1981); nucleoside H-phosphonate method (Garegg et al., 1986; Froehler et al., 1986, Garegg et al., 1986, Gaffney et al., 1988). These chemistries can be performed by a variety of automated nucleic acid synthesizers available in the market. These nucleic acids may be referred to as synthetic nucleic acids. Alternatively, AON's can be produced on a large scale in plasmids (see Sambrook, et al., 1989). AON's can be prepared from existing nucleic acid sequences using known techniques, such as those employing restriction enzymes, exonucleases or endonucleases. AON's prepared in this manner may be referred to as isolated nucleic acids.

For use in vivo, the AONs may be or are stabilized. A "stabilized" AON refers to an AON that is relatively resistant to in vivo degradation (e.g. via an exo- or endo-nuclease). Stabilization can be a function of length or secondary structure. Alternatively, AON stabilization can be accomplished via phosphate backbone modifications. Preferred stabilized AON's of the instant invention have a modified backbone, e.g. have phosphorothioate linkages to provide maximal activity and protect the AON from degradation by intracellular exo- and endo-nucleases. Other possible stabilizing modifications include phosphodiester modifications, combinations of phosphodiester and phosphorothioate modifications, methylphosphonate, methylphosphorothioate, phosphorodithioate, p-ethoxy, and combinations thereof. Chemically stabilized, modified versions of the AON's also include "Morpholinos" (phosphorodiamidate morpholino oligomers, PMOs), 2'-O-Met oligomers, tricyclo (tc)-DNAs, U7 short nuclear (sn) RNAs, or tricyclo-DNA-oligoantisense molecules (U.S. Provisional Patent Application Ser. No. 61/212,384 For: Tricyclo-DNA Antisense Oligonucleotides, Compositions and Methods for the Treatment of Disease, filed Apr. 10, 2009, the complete contents of which is hereby incorporated by reference. Other forms of AONs that may be used to this effect are AON sequences coupled to small nuclear RNA molecules such as U1 or U7 in combination with a viral transfer method based on, but not limited to, lentivirus or adeno-associated virus (Denti, M A, et al, 2008; Goyenvalle, A, et al, 2004). Additionally, the use of AONs, either in their different chemical presentations, or coupled to small nuclear RNA molecules such as U1 or U7 in combination with a viral transfer method, may be combined with a cell therapy approach (i.e. in combination with muscle progenitor/stem cells; or other cell types presenting the capacity of muscle tissue regeneration such as AC133 cells).

In another particular embodiment, the antisense oligonucleotides of the invention are 2'-O-methyl-phosphorothioate nucleotides.

Methods of Treatment and Pharmaceutical Compositions

A further object of the present invention relates to a method for treating a dysferlinopathy caused by a dysfunction of a mutated dysferlin in a patient in need thereof, comprising the step of administering to said patient antisense oligonucleotides complementary to nucleic acid sequences that are necessary for correct splicing of one or more exons which encode amino acid sequences that cause said dysfunction, said antisense oligonucleotides being administered in an amount sufficient to cause skipping of said one or more exons during splicing.

In a particular embodiment, the invention relates to said method wherein antisense oligonucleotides are complementary to nucleic acid sequences that are necessary for correct splicing of a region comprising or consisting of exon 32 of DYSF gene.

In a more particular embodiment, said antisense oligonucleotide is complementary to the nucleic acid sequence SEQ ID NO:1 or SEQ ID NO:2.

In another particular embodiment of the invention, said patient harbours a mutation in exon 32 of DYSF gene. Said mutation leads to a dysferlin dysfunction in said patient.

The invention further relates to an antisense oligonucleotide of the invention for the treatment of dysferlinopathies.

The present invention also provides a pharmaceutical composition containing an antisense oligonucleotide of the invention for the treatment of a dysferlinopathy.

In addition to AONs, pharmaceutical compositions of the present invention may also include a pharmaceutically or physiologically acceptable carrier such as saline, sodium phosphate, etc. The compositions will generally be in the form of a liquid, although this need not always be the case. Suitable carriers, excipients and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, celluose, water syrup, methyl cellulose, methyl and propylhydroxybenzoates, mineral oil, etc. The formulations can also include lubricating agents, wetting agents, emulsifying agents, preservatives, buffering agents, etc. In particular, the present invention involves the administration of AONs and is thus somewhat akin to gene therapy. Those of skill in the art will recognize that nucleic acids are often delivered in conjunction with lipids (e.g. cationic lipids or neutral lipids, or mixtures of these), frequently in the form of liposomes or other suitable micro- or nano-structured material (e.g. micelles, lipocomplexes, dendrimers, emulsions, cubic phases, etc.).

The compositions of the invention are generally administered by injection, e.g. intravenously, subcutaneously or intramuscularly, although other types of administration are not precluded, e.g. inhalation, topical, etc. Injectable preparations, for example, sterile injectable aqueous or oleaginous suspensions may be formulated according to the known art using suitable dispensing or wetting agents and suspending agents. The sterile injectable preparation can also be a sterile injectable solution or suspension in a nontoxic parenterally acceptable diluent or solvent, for example, as a solution in 1,3-butanediol. While delivery may be either local (i.e. in situ, directly into tissue such as muscle tissue) or systemic, usually delivery will be local to affected muscle tissue, e.g. to skeletal muscle, smooth muscle, heart muscle, etc. Depending on the form of the AONs that are administered and the tissue or cell type that is targeted, techniques such as electroporation, sonoporation, a "gene gun" (delivering nucleic acid-coated gold particles), etc. may be employed.

One skilled in the art will recognize that the amount of an AON to be administered will be an amount that is sufficient to induce amelioration of unwanted disease symptoms. Such an amount may vary inter alia depending on such factors as the gender, age, weight, overall physical condition, of the patient, etc. and may be determined on a case by case basis. The amount may also vary according to the type of condition being treated, and the other components of a treatment protocol (e.g. administration of other medicaments such as steroids, etc.). Generally, a suitable dose is in the range of from about 1 mg/kg to about 100 mg/kg, and more usually from about 2 mg/kg to about 10 mg/kg. If a viral-based delivery of AONs is chosen, suitable doses will depend on different factors such as the viral strain that is employed, the route of delivery (intramuscular, intravenous, intra-arterial or other), but may typically range from 10e10 to 10e12 viral particles/kg. Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the recipient. In addition, treatment of the patient is usually not a single event. Rather, the AONs of the invention will likely be administered on multiple occasions, that may be, depending on the results obtained, several days apart, several weeks apart, or several months apart, or even several years apart. This is especially true where the treatment of dysferlinopathy is concerned since the disease is not cured by this treatment, i.e. the gene that encodes the protein will still be defective and the encoded protein will still possess an unwanted, destabilizing feature such as an exposed proteolytic recognition site, unless the AONs of the invention are administered.

The treating methods of the present invention can be implemented in any of several different ways. For example, the AONs of the present invention may be administered together with AONs designed to remove other exons (e.g. in a single mixture, or in separate mixtures but administered in close temporal proximity, such as one directly after the other-in any order-with only a few minutes or hours between administrations). Alternatively, a patient who is already under treatment using e.g. exon skipping or stop codon read-through protocols may be treated by the methods of the invention. In other words, the AONs of the invention may be administered to a patient who is already or has been receiving another treatment, but is still in need of further amelioration of the functional capabilities of the dysferlin molecules produced as a result of the other treatment.

If the AONs of the present invention are to be administered with AONs designed to skip exons for purposes other than to eliminate a protease recognition site, one possible route of administration is to include sequences encoding from both types of AONs (those designed to eliminate one or more exons encoding one or more protease recognition sites and those designed to eliminate exons for another reason) in a single vector that is administered to a patient. Those of skill in the art will recognize that several vectors are available for use in delivering nucleic acid sequences so that the nucleic acid sequences may be transcribed in vivo within the recipient. Examples of such vectors include but are not limited to various vectors derived from attenuated viruses such as retroviral vectors, adenoviral vectors, adeno-associated viral vectors, HIV and influenza virus vectors, etc. Vectors based on attenuated bacteria might also be employed, e.g. mycobacterial based vectors. Those of skill in the art will recognize that if these types of methods are used, it may be preferable to avoid multiple administrations which could result in an adverse immune response to the vector.

The individuals or patients treated by the methods described herein are typically mammals, usually humans. Veterinary applications of this technology are also contemplated.

The invention will be further illustrated by the following figures and examples. However, these examples and figures should not be interpreted in any way as limiting the scope of the present invention.

FIGURES

FIG. 1: Human dysferlin exon map and phasing. a) Representation of the 55 exons of the human dysferlin gene (blue). Red boxes correspond to the 5' and 3' UTR. On top of each exon, the length in base pairs is indicated. Inside the boxes the position of the first and last residue is written in red. Below each exon the bioinformatics predictions of protein domains are represented (ScanProsite solid line and Pfam dotted line). The intron lengths are mentioned between the exons. The genetic defect in the dysferlin gene of three mouse models are depicted on the scheme. The phasing was performed using the UMD-DYSF database, a specific database generated on a similar model, as compared to UMD-DMD (Tuffery-Giraud et al., 2009). b) Schematic representation of exon 32 and surrounding sequences. The selected 2'O-methyl phosphorothioate oligonucleotide (AON) are indicated below the sequence. These AON blocked either the branching point (BP) or exonic splicing enhancers (predicted using Human Splicing Finder) (Desmet, et al., 2009) (ESE1) or using ESE finder 3.0 (ESE2). The Asterisk indicates the mutated nucleotide in patient F1-38-1-2.

FIG. 2: Dysferlin exon 32 skipping analysis. a) RT-PCR analysis of the transcript region flanking exon 32 (exons 30 to 33) in control fibroblast-derived myoblasts. After treatment with AON ESE1 or ESE2, a shorter transcript fragment, not present in the control or RNA from cells treated with AON BP1, was observed at the expected size (215 bp). Sequence analysis of the RT-PCR fragment identified the correct skipping of dysferlin exon 32 and the exact junction between exons 31 and 33. b) Fibroblast-derived myoblasts from Patient F1-38-1-2 were treated with both AON targeting ESE sequences. c) Infection of U7-smOPT-ESE2ESE1 at an MOI $(2.25\ 10^4)$ in human control myoblasts (CHQ) evidenced the same skipping as observed with AON although at a lower efficiency. When the MOI was doubled the signal was increased. Sequence analysis of the RT-PCR fragment shows the correct skipping of exon 32. No additional splice variants were observed when a PCR encompassing exon 30 to 37 (lower panel) was used instead of the 30-33 PCR. d) Transduction of patient F1-38-1-2 fibroblast-derived myoblasts with U7-smOPT-ESE2ESE1 at a MOI (2.25 10$^4$) evidenced the 32-DYSF transcript. RT-: RT-PCR reaction without RT; Control: positive reaction using the full length dysferlin cDNA as template.

EXAMPLE

Materials and Methods

Skin fibroblast and myoblast cultures. All experiments and biopsies were carried-out in accordance with the ethical rules of the institutions involved. Patient fibroblast cultures were derived from a skin biopsy obtained from a patient affected with Miyoshi myopathy (Patient F1-38-1-2: compound heterozygous c.3477C>A [exon 32, p.Tyr1159X] and c.5979dupA [exon 53, p.Glu1994ArgfsX3]). Mutational data are described using the nomenclature of the Human Genome Variation Society (www.hgvs.org/mutnomen). Nucleotide numbering reflects cDNA numbering with +1 corresponding to the A of the ATG translation initiation codon in the reference sequence (human DYSF, GenBank NM_003494.2), according to journal guidelines. The initiation codon is codon 1.

Control myoblasts (CHQ) were derived from a quadriceps biopsy performed on a 5 day old donor, as already described (Edom, et al., 1994). All culture media and reagents were obtained from Gibco (Invitrogen, Paisley, UK). Primary human cells were extracted from biopsies by enzymatic dissociation with collagenase 1A (Sigma-Aldrich, St. Louis, Mo., USA). Cells were expanded in the proliferation medium composed of DMEM (Gibco), 20% Fetal Bovine serum (PAA Laboratories GmbH, Pasching, Austria), 100 µg/ml penicillin, 100 µg/ml streptomycin (Biowest, Nuaille, France), and L-glutamin (Gibco). At confluence, cells were cultured in the differentiation medium composed of DMEM supplemented with Glutamax and 1 mM pyruvate sodium (Gibco), 2% Horse serum (Gibco), 10 µg/ml insulin (Sigma-Aldrich), 100 µg/ml apotransferrin (Sigma-Aldrich), 100 µg/ml penicillin, 100 µg/ml streptomycin, and L-glutamine (Chaouch, et al., 2009)

Identification of Target Sequences for Dysferlin Exon 32 Skipping. Bioinformatics analyses to find targetable sequences within exon 32 of the DYSF gene and its surrounding intronic sequences, were realized using www.umd.be/HSF/ and http://rulai.cshl.edu/cgi-bin/tools/ESE3/esefinder.cgi?process5home).

Figure 1A:
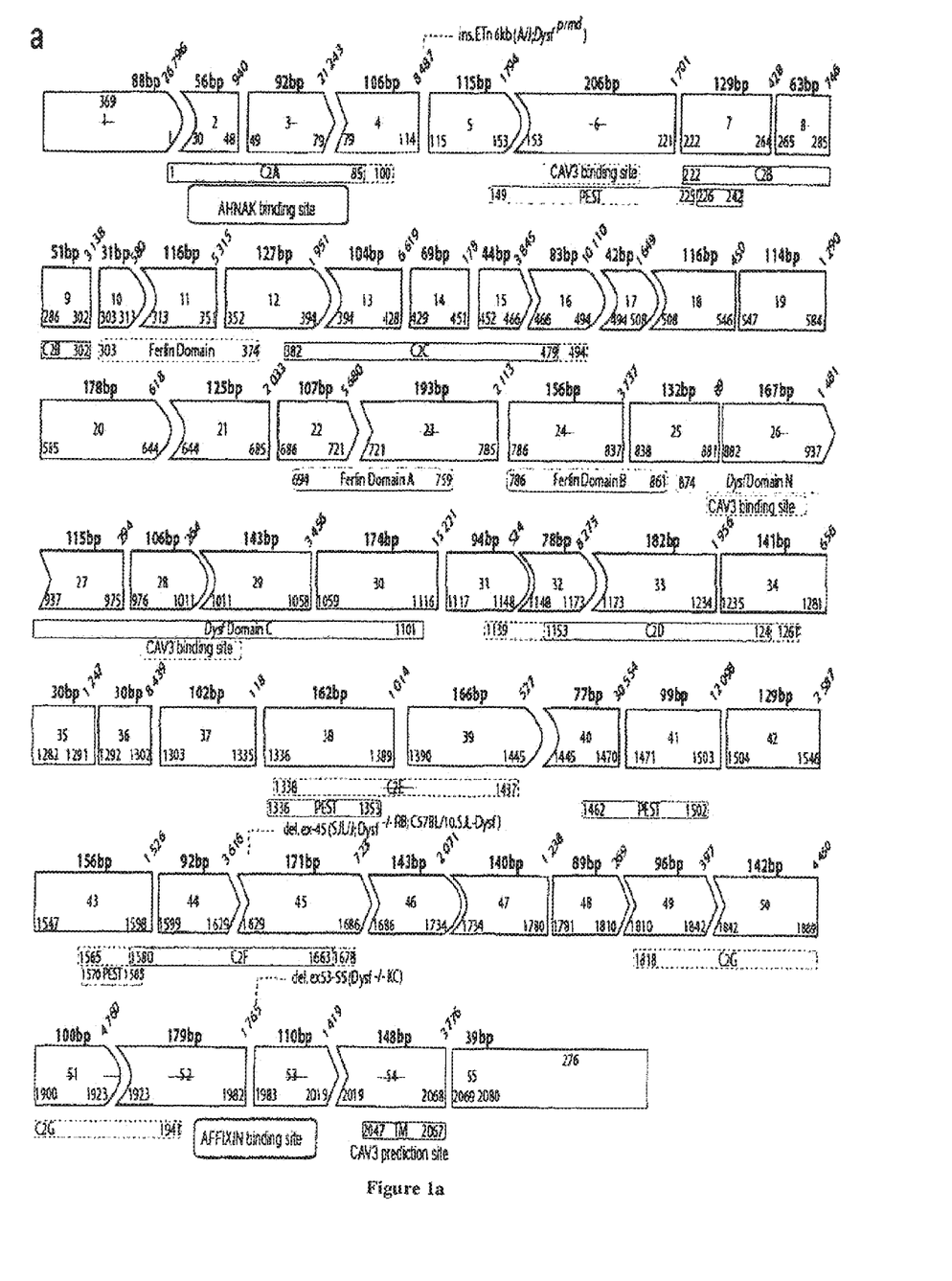

AONs and transfection. Exonic splicing enhancer (ESE) and exonic splicing silencer (ESS) sequences were identified by Human Splicing Finder (Desmet, et al., 2009) and ESE finder 3.0 (Cartegni and Krainer, 2003; Smith, et al., 2006). The corresponding selected sequences are represented in FIG. 1. All AONs were synthesized by Eurogentec (Seraing, Belgium) and contain 2'-O-methyl RNA and full-length phosphorothioate (PS) backbones. Fibroblast-derived myoblast cultures were transfected using Oligofectamin (Invitrogen) according to the manufacturer's instructions. Each AON was transfected twice at 10 µg/µl in at least two separate experiments. A control AON with a 5' fluorescein label was used to ascertain optimal transfection, efficiencies were evaluated by counting the number of fluorescent nuclei (over 90% of all nuclei were labelled). RNA was isolated 48 hours post-transfection.

Vector construction and production. a) U7 snRNA. The U7 DNA constructs were engineered from the previously described U7SmOPT; where the original Sm binding domain is replaced by an optimized U2 type binding domain (Gorman, et al., 1998) and antisense sequence targeting the histone pre-mRNA is replaced by specific antisense sequences targeting splicing sequences within the human pre mRNA of dysferlin (FIG. 1). The constructions U7smOPT-ESE1, U7smOPT-ESE2, U7smOPT-ESE1-ESE2 and U7smOPT-ESE2-ESE1 fragments were subcloned into a plasmid pRRL-cPPT-mcs-WPRE, derived from the pRRL-cPPT-hPGK-eGFP-WPRE construct (Naldini, 1998). Constructs were sequenced on an ABI3130x1 Genetic Analyzer (Applied Biosystems, Carlsbad, Calif., USA) and analyzed with Sequencher software (Gene Codes Corporation, Ann Arbor, Mich., USA). b) MyoD. The mouse MyoD cDNA was inserted into the tet-on inducible lentiviral construct previously described containing the tet-responsive transactivator rtTA2S-M2 inducing the MyoD expression in the presence of doxycycline (Barde, et al., 2006). c) Production. As previously described, lentiviral vectors pseudotyped with the VSV-G protein were produced by transient quadri-transfection into 293T cells (Coriell Cell Repository; Camden, N.J., USA) and the viral titers (infectious particles) were determined by transduction of HCT116 cells and assayed by quantitative real-time PCR on genomic DNA (Charrier, et al., 2005). Titration of the 4 lentivirus is expressed as viral genome per ml (vg/ml) (ranging from $4.5 \times 10^8$ to $2.4 \times 10^9$ vg/ml).

Lentiviral vector transduction of fibroblasts. For Myo-D induction of fibroblasts, $2 \times 10^3$ to $6 \times 10^3$ cells/cm$^2$ were plated into gelatin B (Sigma) pre-coated wells. At about 70% confluence, 2 to $5 \cdot 10^9$ vg/ml lentivirus were added into 500 µl of DMEM medium, diluted four hours later into 500 µl of the proliferation medium. To induce MyoD expression, doxycycline (10 µg/ml) (Sigma) was added at about 80% confluence and subsequently, at full confluence, the proliferation medium was replaced by the differentiation medium supplemented with doxycycline (10 µg/ml). MyoD-induced expression of specific myogenic markers was evaluated by RT-PCR after doxycycline induction. Transduction of fibroblast derived myoblasts and CHQ cells (Edom, et al., 1994) with U7smOPT-ESE1, U7smOPT-ESE2, U7smOPT-ESE1-ESE2 and U7smOPT-ESE2-ESE1 lentiviral vectors was carried out using the same protocol (Chaouch, et al., 2009).

RNA extraction and classical and nested PCR. RNAs were extracted from cultured cells using RNeasy kit and mRNA were purified with a poly dT column (Qiagen, Courtaboeuf, France). One µg of mRNA was reverse transcribed into cDNA with the Super-Script II RT (Invitrogen) primed by random hexamers according to the manufacturer. PCR amplifications were performed with 1 µg of RT-product using primer pairs flanking the targeted exons (sequences available upon request) for 35 cycles. Dysferlin RNA exon skipping was analyzed by classical RT-PCR for AONs study and nested RT-PCR for U7 lentiviral transduction study. The products of PCR were separated by electrophoresis in a 1.5% agarose gel stained with ethidium bromide. The PCR product was then gel extracted using NucleoSpin extract II (Macherey-Nagel GmbH & Co KG, Düren, Germany) and sequenced using the Big Dye Terminator Cycle Sequencing Kit (Applied Biosystem, Courtaboeuf, France).

Immunoblot. Detection of dysferlin was performed using standard protocols with primary dysferlin antibodies (NCL-Hamlet, Novocastra, Newcastle-upon-Tyne, UK) diluted 1/300 on patient MyoD transduced fibroblasts protein extracts.

Immunofluorescence. Labeling of dysferlin was performed according to Wein et al., 2010. Cells were grown on Lab-Tek™ (Nunc, Fischer scientific) and fixed with 4% of paraformaldehyde for 10 min. Cells were then incubated for 30 min with blocking solution (PBS+10% HNS+10 μg/mL of human IgG Fc fragment) and permeabilized for 10 min with 150 μl of permeabilization solution (PBS+10% HNS+0.1% triton X-100 (Sigma-Aldrich). On each sample slide (patient samples and control sample in parallel), 100 μl of primary antibody solution (PBS+10% HNS+1/50e NCL-Hamlet) were added. In the same time, on control slide, 100 μl of isotype solution (PBS+10% HNS+Nim(Jackson Immunoresearch)) was added overnight at 4° C. or for 2 h at RT. After 5 washes with PBS, 100 μl of secondary antibody solution were added on all slides (PBS+10% HNS+1/400e alexa488) and incubated 1 h at RT. After 5 washes with PBS, 100 μl of DAPI solution was added for 15 min (50 ng/mL DAPI (Invitrogen)+PBS). After 5 washes with PBS, the slides were dried and mounted with (Vectashield). Observation was realized using Leica™ DMR (Wetzlar). Acquisitions were taken using CoolSnap camera (Roper Scientific).

Membrane Wounding Assay. To induce damage, an area of the sarcolemma on the membrane of the myotubes was irradiated at full power for 1 second with a two-photon confocal laser-scanning microscope. The Multi-Photon apparatus consisted of a mode-locked Titanium-Sapphire laser system tuned to a 1035 nm excitation with 100 fs pulses at 76 MHz. The microscope was an inverted LEICA SP3. Images were captured for 3 min after the irradiation at 7-s intervals. For every image taken, the fluorescence intensity at the site of the damage will be measured by ImageJ on an area of about 0.01 $mm^2$ and plotted on a graph with the time on the x-axis and the amount of fluorescence on the y-axis.

Results

Figure 1B:
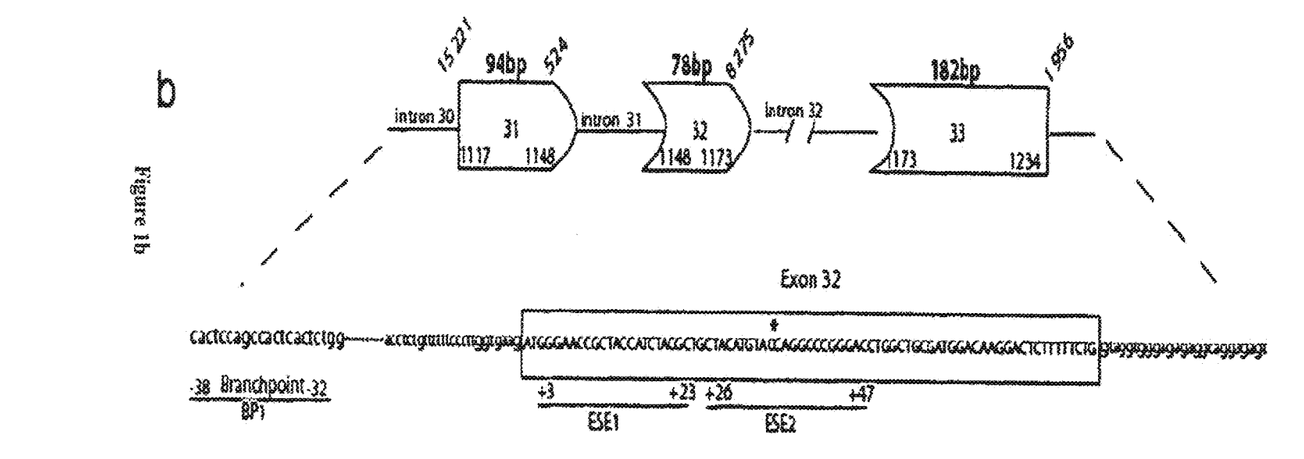

Identification of target sequences for dysferlin exon 32 skipping. We performed bioinformatics analyses in order to find targetable sequences within exon 32 of the DYSF gene and its surrounding intronic sequences. Various sequences such as exon splicing enhancers (ESE) are recognized by specific splicing proteins and are required to maintain exons within mRNAs. If some of these sequences are masked or absent, the targeted exon is skipped (Aartsma-Rus, et al., 2004). According to the bioinformatics analyses performed (www.umd.be/HSF/ and http://rulai.cshl.edu/cgi-bin/tools/ESE3/esefinder.cgi?process=home) (Cartegni and Krainer, 2003; Desmet, et al., 2009; Smith, et al., 2006), two sequences reached an ESE significant score, while a third sequence was identified as containing the lariat branch point in intron 31. These sequences were selected to be further targeted with 2'O-methyl phosphorothioate (PS) antisense oligonucleotides (AON) (FIG. 1b).

Figure 2:
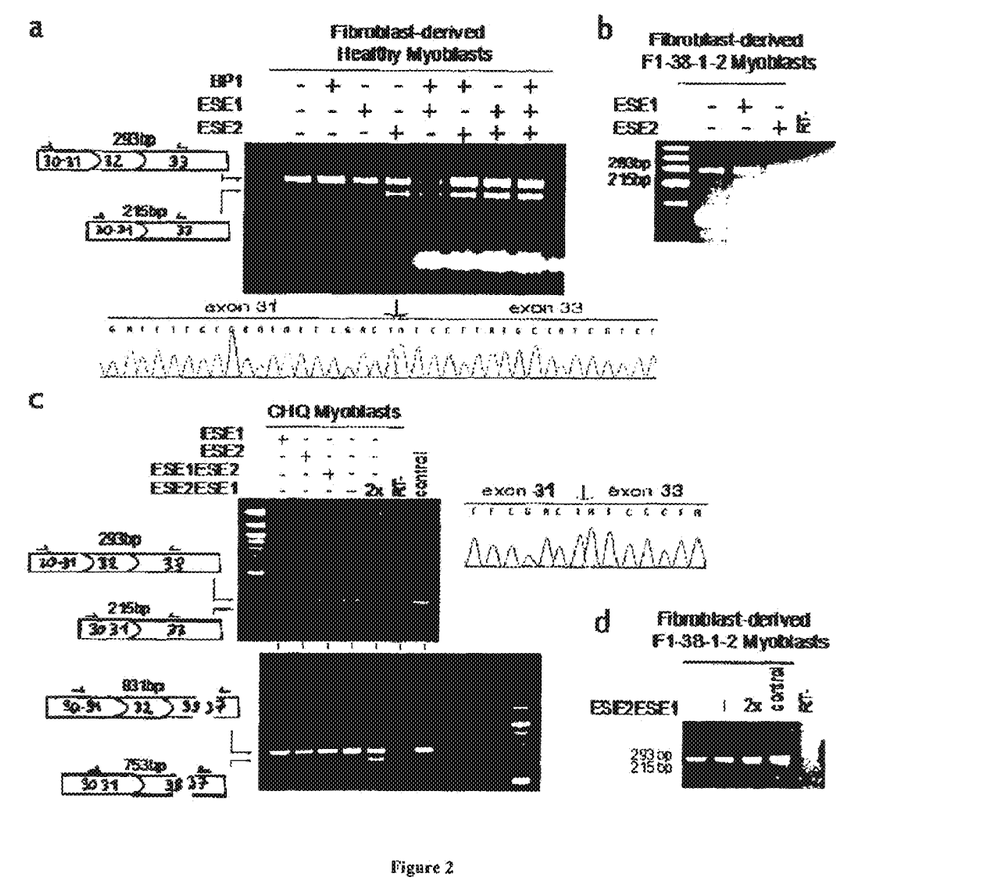

Skipping of dysferlin exon 32 is efficient in myoblasts. Fibroblasts from a control subject were transduced by an inducible construct harbouring the MyoD gene and converted to fibroblast-derived myoblasts upon induction of MyoD expression. They were transfected with the different AON (BP, ESE1, ESE2) combined with oligofectamine. RT-PCRs with forward primers in exon 30 and reverse primers in exon 33 evidenced a skipping of the DYSF-exon 32 (Δ32) with the AON targeting the predicted ESE sites (FIG. 2a). Two bands were detected, one corresponding to the wild type transcript containing exon 32 (293 bp) and another corresponding to the Δ 32 skipped mRNA (215 bp), as confirmed by sequencing. No skipping was observed with the AON targeted against the lariat branchpoint only.

Subsequently, fibroblast-derived myoblasts from one patient (Patient F1-38-1-2: compound heterozygous c.3477C>A [exon 32, p.Tyr1159X] and c.5979dupA [exon 53, p.Glu1994ArgfsX3]) were treated as described above. Targeted transcriptional analysis of the patient's sample treated with ESE1, revealed a shorter transcript indicating the skipping of exon 32 (FIG. 2b). In contrast, no skipping was observed when ESE2 was used. An exon 32 containing transcript was identified from untreated fibroblast-derived myoblasts from this patient, indicating it escaped the nonsense mediated mRNA decay mechanism although, in this situation, the intensity of the 293 bp product was lower. For ESE2, it is likely that, since the mutation is within its recognition site, this would confer a lower efficiency than the ESE1 AON. Therefore, due to this weak level of transcription, the skipped transcript was not observed.

Lentiviral-induced skipping of dysferlin exon 32. In order to confirm the possibility to skip exon 32 in patient's cells, we developed a lentiviral approach which would be more suited if a cell based therapy using corrected myogenic stem cells appears as a valuable clinical approach, as already suggested for other diseases such as Duchenne muscular dystrophy (Benchaouir et al, 2007). For this purpose, stem cell populations could be transduced with a lentiviral vector expressing the U7-snRNA containing antisense sequences designed to specifically skip exon 32 and restore dysferlin expression. Moreover, although the lentiviral based approach cannot be strictly extrapolated to other vectors and cell types, such a strategy could be used in different cell types expressing dysferlin, in particular monocytes, expressing a high level of dysferlin, which are easier and less invasive to obtain than myoblasts. We designed four different lentiviral vectors harboring a cassette containing antisense sequences for the skipping of exon 32 from the dysferlin pre-mRNA. We used cassettes containing the selected sequences ESE1 and ESE2 either alone or in cis combination in the same vector (ESE1-ESE2 and ESE2-ESE1). To test whether this strategy would efficiently induce skipping of exon 32 in vitro, human control myoblasts (CHQ) were transduced with the U7 exon 32 lentiviral vectors. mRNAs were collected and analyzed by nested RT-PCR. A fragment corresponding to the expected size after skipping of exon 32 was observed from cells transduced with the U7smOPT-ESE2-ESE1 vector at a multiplicity of infection (MOI) of $2.25 \cdot 10^4$; this signal intensity was positively correlated with the MOI (FIG. 2c, upper panel). Efficient and specific skipping was further confirmed by direct sequencing of the RT-PCR products (FIG. 2c). No signal was observed in all other conditions (FIG. 2c). To ensure the specificity of exon 32 skipping, subsequent PCR experiments were conducted using primers in exons 30 (forward primer) and 37 (reverse primer) on the same samples. An identical pattern of skipping was observed without additional bands thus excluding aberrant splicing in the analyzed region (FIG. 2c lower panel). Identical results were obtained when the same lentivirus was used to transduce fibroblast-derived myoblasts from healthy control.

Fibroblast-derived myoblasts obtained from patient F1-38-1-2 were then transduced by the U7smOPT-ESE2-ESE1 lentivirus vectors (FIG. 2d). Transduced cells expressed a significant amount of Δ32-DYSF as revealed by RT-PCR.

Functionality of the quasi-dysferlin deleted of exon 32. To test the functionality of this quasi-dysferlin deleted of exon 32, we have synthesized a new AON that masks the donor site of exon 32 (AON +63-6) AOND. We transfected AON in fibroblasts of patients transdifferenciated into myotubes, RNA extraction was performed and allowed us to show the presence of transcripts deleted of exon 32. In particular, the AON D is capable of forcing the skipping of exon 32 with an efficiency of 75%. In view of its high efficiency the AON D was used in subsequent studies.

Before studying the functionality of the quasi-dysferlin, we wanted to highlight the production of this protein after treatment. However, as exon 32 encodes only 26 aa, the difference in migration between dysferlin and quasi-dysferlin can not be detected by WB in treated fibroblasts controls. So we had to carry out all the following experiments on cells from patients. Thus, after transfection of AONs in patients' cells we were able to demonstrate the expression of a protein at the expected size, but in small proportion after the treatment with the AON D. Given the lack of specificity and efficiency of the antibody used, it is possible that the method for demonstrating the quasi-dysferlin might be not enough sensitive. These are encouraging results. To verify the existence of this quasi-dysferlin and localization, immunostaining experiments were performed on fibroblasts of patients treated with AON D. These experiments suggest the presence of a protein localized in both the cytoplasm and at the plasma membrane in treated cells. To test the involvement of dysferlin in the membrane repair mechanisms, the main function identified for dysferlin, we adapted the protocol of membrane repair assay for use on human cells in culture. We were able to demonstrate that the cells of patients after treatment with AON were more likely to repair the membranes than the non treated cells. In particular, the use of AON D, which was most effective in inducing exon skipping, allows efficient membrane repair. Taken together, these results demonstrate that in patients with mutation in exon 32, the skipping of exon 32 allows the synthesis of a quasi-dysferlin that can repair the membrane of muscle cells.

References

Throughout this application, various references describe the state of the art to which this invention pertains. The disclosures of these references are hereby incorporated by reference into the present disclosure.

Barde I, Zanta-Boussif M A, Paisant S, Leboeuf M, Rameau P, Delenda C, Danos O. 2006. Efficient control of gene expression in the hematopoietic system using a single Tet-on inducible lentiviral vector. Mol Ther 13(2):382-90.

Beaucage, S. L., and Caruthers, M. H., Tet. Let. 22:1859, 1981.

Beroud C, Tuffery-Giraud S, Matsuo M, Hamroun D, Humbertclaude V, Monnier N, Moizard M P, Voelckel M A, Calemard L M, Boisseau P and others. 2007. Multiexon skipping leading to an artificial DMD protein lacking amino acids from exons 45 through 55 could rescue up to 63% of patients with Duchenne muscular dystrophy. Hum Mutat 28(2):196-202.

Chaouch S, Mouly V, Goyenvalle A, Vulin A, Mamchaoui K, Negroni E, Di Santo J, Butler-Browne G, Torrente Y, Garcia L and others. 2009. Immortalized Skin Fibroblasts Expressing Conditional MyoD as a Renewable and Reliable Source of Converted Human Muscle Cells to Assess Therapeutic Strategies for Muscular Dystrophies: Validation of an Exon-Skipping Approach to Restore Dystrophin in Duchenne Muscular Dystrophy Cells. Hum Gene Ther.

Charrier S, Stockholm D, Seye K, Opolon P, Taveau M, Gross D A, Bucher-Laurent S, Delenda C, Vainchenker W, Danos O and others. 2005. A lentiviral vector encoding the human Wiskott-Aldrich syndrome protein corrects immune and cytoskeletal defects in WASP knockout mice. Gene Ther 12(7):597-606.

De Luna N, Freixas A, Gallano P, Caselles L, Rojas-Garcia R, Paradas C, Nogales G, Dominguez-Perles R, Gonzalez-Quereda L, Vilchez J J and others. 2007. Dysferlin expression in monocytes: a source of mRNA for mutation analysis. Neuromuscul Disord 17(1):69-76.

Denti M A et al., Hum Gene Ther. 19(6):601-8, 2008.

Edom F, Mouly V, Barbet J P, Fiszman M Y, Butler-Browne G S. 1994. Clones of human satellite cells can express in vitro both fast and slow myosin heavy chains. Dev Biol 164(1): 219-29.

Desmet F O, Hamroun D, Lalande M, Collod-Beroud G, Claustres M, Beroud C. 2009. Human Splicing Finder: an online bioinformatics tool to predict splicing signals. Nucleic Acids Res 37(9):e67.

Froehler et al., Nucl. Acid. Res. 14:5399-5407, 1986

Gaffney et al., Tet. Let. 29:2619-2622, 1988

Garegg et al., Tet. Let. 27:4051-4054, 1986

Garegg et al., Tet. Let. 27:4055-4058, 1986

Gorman L, Suter D, Emerick V, Schumperli D, Kole R. 1998. Stable alteration of pre-mRNA splicing patterns by modified U7 small nuclear RNAs. Proc Natl Acad Sci USA 95(9):4929-34.

Goyenvalle A et al., Science, 306(5702):1796-9. 2004

Krahn M, Beroud C, Labelle V, Nguyen K, Bernard R, Bassez G, Figarella-Branger D, Fernandez C, Bouvenot J, Richard I and others. 2009a. Analysis of the DYSF mutational spectrum in a large cohort of patients. Hum Mutat 30(2):E345-75.

Naldini L. 1998. Lentiviruses as gene transfer agents for delivery to non-dividing cells. Curr Opin Biotechnol 9(5): 457-63.

Sambrook, T., et al., Cold Spring Harbor laboratory Press, New York, 1989

Sinnreich M, Therrien C, Karpati G. 2006. Lariat branch point mutation in the dysferlin gene with mild limb-girdle muscular dystrophy. Neurology 66(7):1114-6.

Therrien C, Dodig D, Karpati G, Sinnreich M. 2006. Mutation impact on dysferlin inferred from database analysis and computer-based structural predictions. J Neurol Sci 250(1-2):71-8.

The invention claimed is:

1. A method for restoring the function of a mutated dysferlin in a subject comprising the step of preventing splicing of one or more exons which encode amino acid sequences that cause said dysferlin dysfunction by providing said subject one or more antisense oligonucleotides complementary to nucleic acid sequences that are necessary for correct splicing of said one or more exons which encode amino acid sequences that cause said dysferlin dysfunction, said one or more antisense oligonucleotides being provided in an amount sufficient to cause skipping of said one or more exons during splicing,
 wherein said one or more antisense oligonucleotides are complementary to nucleic acid sequences that are necessary for correct splicing of a region comprising exon 32 of the DYSF gene, and
 wherein said one or more antisense oligonucleotides are complementary to the nucleic acid sequence SEQ ID NO:1 or SEQ ID NO:2.

2. An antisense RNA oligonucleotide complementary to a nucleic acid sequence of the DYSF gene that is necessary for correct splicing of one or more exons which encode an amino acid sequence of dysferlin implicated in dysfunction of a mutated dysferlin,
 wherein said antisense oligonucleotide is complementary to a nucleic acid sequence comprising exon 32 of the DYSF gene or nucleic acid sequences required for correct splicing of a region comprising exon 32 of the DYSF gene, and
 wherein said antisense oligonucleotide is complementary to the nucleic acid sequence SEQ ID NO:1 or SEQ ID NO:2.

3. A method for treating a dysferlinopathy caused by a dysfunction of a mutated dysferlin in a patient in need thereof, comprising the step of administering to said patient one or more antisense oligonucleotides complementary to nucleic acid sequences that are necessary for correct splicing of one or more exons which encode amino acid sequences that cause said dysfunction, said one or more antisense oligonucleotides being administered in an amount sufficient to cause skipping of said one or more exons during splicing,
 wherein said one or more antisense oligonucleotides are complementary to nucleic acid sequences that are necessary for correct splicing of a region comprising exon 32 of the DYSF gene, and
 wherein said one or more antisense oligonucleotides are complementary to the nucleic acid sequence SEQ ID NO:1 or SEQ ID NO:2.

4. The method of claim 3, wherein said patient harbours a mutation in exon 32 of the DYSF gene.

5. A pharmaceutical composition for the treatment of a dysferlinopathy, comprising
 the antisense oligonucleotide of claim 2 and
 a pharmaceutically acceptable carrier.

* * * * *